United States Patent [19]
Marui

[11] Patent Number: 5,371,366
[45] Date of Patent: Dec. 6, 1994

[54] ION SCATTERING SPECTROSCOPE
[75] Inventor: Takao Marui, Hadano, Japan
[73] Assignee: Shimadzu Corporation, Kyoto
[21] Appl. No.: 77,366
[22] Filed: Jun. 17, 1993
[30] Foreign Application Priority Data
Jun. 30, 1992 [JP] Japan .................. 4-173351
[51] Int. Cl.⁵ .......................... H01J 37/252
[52] U.S. Cl. .................. 250/309; 250/305; 250/287; 250/307
[58] Field of Search ............... 250/309, 307, 305; 287
[56]   References Cited
U.S. PATENT DOCUMENTS
5,182,453  1/1993  Hayashi ................ 250/309

FOREIGN PATENT DOCUMENTS
0488067A2  6/1992  European Pat. Off. .
0501257A3  9/1992  European Pat. Off. .
63-102150  5/1988  Japan .
2-90049    3/1990  Japan .

OTHER PUBLICATIONS
K. Sumitomo et al; "A TOF–ISS/ERDA Apparatus for Solid Surface Analysis"; *Nuclear Instruments & Methods in Physics Research/Section B;* Jun., 1988; pp. 871–875.

N. Sugiyama et al; "In Situ Analysis of Gallium Arsenide Surfaces by Coaxial Impact Collision Ion-Scattering Spectroscopy with an Off-Axis Ion Source"; *Japanese Journal of Applied Physics 29;* Oct., 1990; pp. L1922–L1925.

M. Katayama et al; "Coaxial Impact–Collison Ion Scattering Spectroscopy (CAICISS): A Novel Method for Surface Structure Analysis"; *Nuclear Instruments and Methods in Physics Research;* 1988; pp. 857–861.

*Primary Examiner*—Jack I. Berman

[57]  ABSTRACT

A time-of-flight (TOF) type ion scattering spectroscope (ISS) using a mixture of ions of different masses. Ions having a mass smaller than the smallest mass of the atoms in the sample surface can precisely discriminate light-weight object atoms of slightly different masses. Ions having an intermediate mass between heavy-weight atoms and light-weight atoms in the sample surface can precisely discriminate heavy-weight object atoms of slightly different masses.

8 Claims, 6 Drawing Sheets

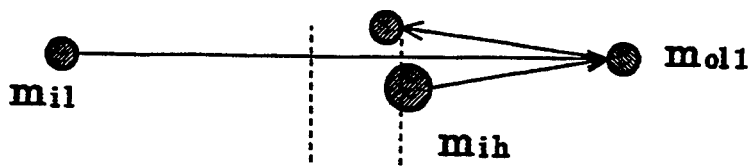
Fig. 6A
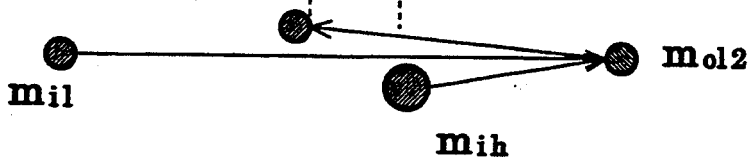
Fig. 6B
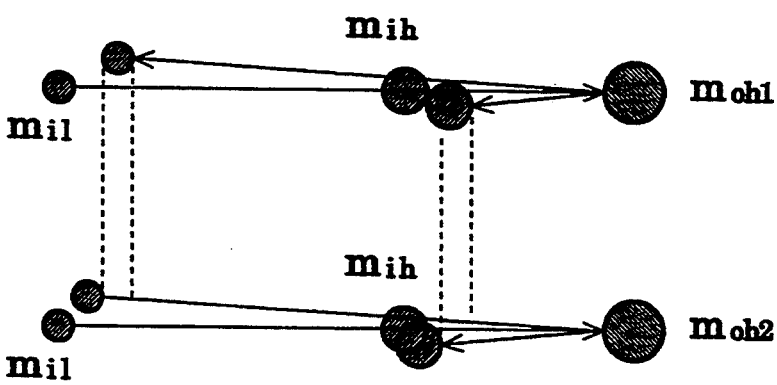
Fig. 6C
Fig. 6D
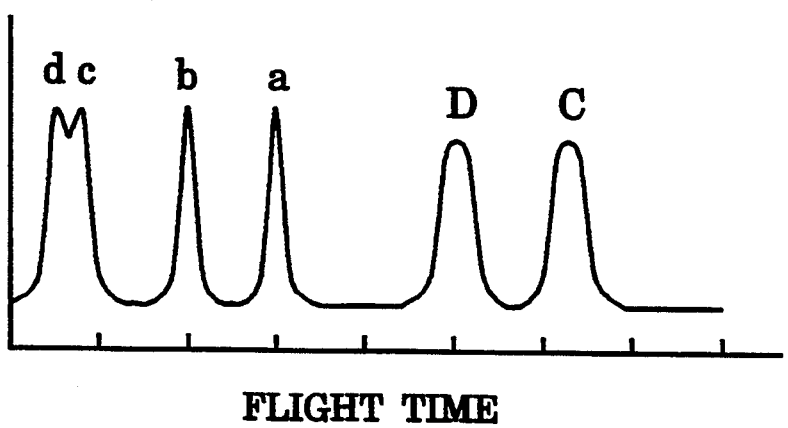
Fig. 6E

ION SCATTERING SPECTROSCOPE

The present invention relates to a time-of-flight (TOF) type ion scattering spectroscope (ISS) for performing a chemical and structural analysis of a surface of a solid sample.

BACKGROUND OF THE INVENTION

In an ion scattering spectroscopy, a beam of ions of a known fixed kinetic energy is irradiated onto a surface of a solid sample, and the energy spectrum of ions colliding with the atoms in the surface or subsurface and scattered within a preset small solid angle is measured. For measuring the energy of the scattered ions, a method known as the time-of-flight (TOF) method is used.

A TOF type ISS is illustrated with FIG. 7. When a beam of ions 46 is irradiated onto a sample 41, the ions collide with the atoms of the sample 41 and are scattered backward. Some of the scattered ions come into a flight tube 43 through the gate 42. The space within the flight tube 43 is a drift space in which no electromagnetic field is present and the ions fly without being exerted by an external force. Since the speed of an ion is proportional to the square root of its energy, the flight time of an ion in the flight tube 43, thus the arriving time of an ion at an ion detector 40 placed at an end of the flight tube 43, depends on the energy of the ion.

The flight time $t_f$ of an ion having mass m and an initial energy E travelling a distance d is given by $$t_f = d \cdot \{m/(2 \cdot E)\}^{\frac{1}{2}}. \quad (1)$$

By measuring the flight time $t_f$ of a scattered ion, its energy E is calculated using the formula (1). When an ion beam injecting onto the sample is pulsated, the starting point of the flight time $t_f$ can be taken from the pulsating timing, and when the injecting beam is continuous, the opening time of the electric field shutter at the gate 42 is used as the starting point of the flight time $t_f$. In the pulsating (chopping) beam method, therefore, the length of time period from the time when the beam of ions is chopped to the time when the ions scattered by the sample surface arrives to the detector is measured, the speed of scattered ions is calculated, and the mass of atoms of the sample that scattered the ions is calculated.

In such a TOF type ISS, an ion generator is provided in which ions involved in the measurement are generated from a solid or gas ion source. Because the mass of ions used in the measurement should correspond to the sample, proper material of the ion source should be selected depending on the sample. The reason is explained referring to FIG. 8. When an ion of mass $m_i$ running at speed $v_1$ collides with a stationary atom of mass $m_o$, the speed $v_2$ of the ion scattered almost 180° backward is given by $$v_2 = (m_o - m_i) \cdot v_1 / (m_o + m_i). \quad (2)$$

If the mass $m_i$ and the speed $v_1$ of the colliding ion is known, the mass $m_o$ of the object atom can be calculated from the formula (2) by measuring the speed $v_2$ of the back-scattered ion.

The formula (2) also teaches that the motion of the ion after the collision depends on the mass of the ion $m_i$ and the mass of the atom $m_o$. When $m_o \gg m_i$, that is the mass $m_o$ of the stationary atom is far larger than the mass $m_i$ of the colliding ion, the speed $v_2$ of the ion after the collision is almost the same as the speed $v_1$ before the collision, and the diversity in the speed of scattered ions is so small that the precision of the measurement is low. When, on the other hand, $m_o \leq m_i$, that is the mass $m_o$ of the stationary atom is comparable to or smaller than the mass $m_i$ of the colliding ion, the ion cannot be scattered backward and no measurement is possible.

It is necessary therefore to use an ion having a mass slightly smaller than that $m_o$ of the object atom to measure the mass $m_o$ of the atom of the sample precisely. This is why the mass of the ions should be properly selected in the measurement, and the material of the ions source is changed according to the sample. If the object element to be measured is changed, further, though the sample remains the same, the ion source should be changed accordingly. The change of the ion source, albeit solid ion source or gas ion source, requires troublesome operations and long measurement-interrupting time.

SUMMARY OF THE INVENTION

The present invention addresses the problem and provides an improved TOF type ion scattering spectroscope which need not such change of ion source according to the object atom.

BRIEF DESCRIPTION OF THE DRAWINGS

FIG. 6A through 6D are diagrams showing mixed-weight ions colliding with light and heavy object atoms, and FIG. 6E is a flight time spectrum (energy spectrum) of the scattered mixed-weight ions.

DETAILED DESCRIPTION OF A PREFERRED EMBODIMENT

Figure 1:
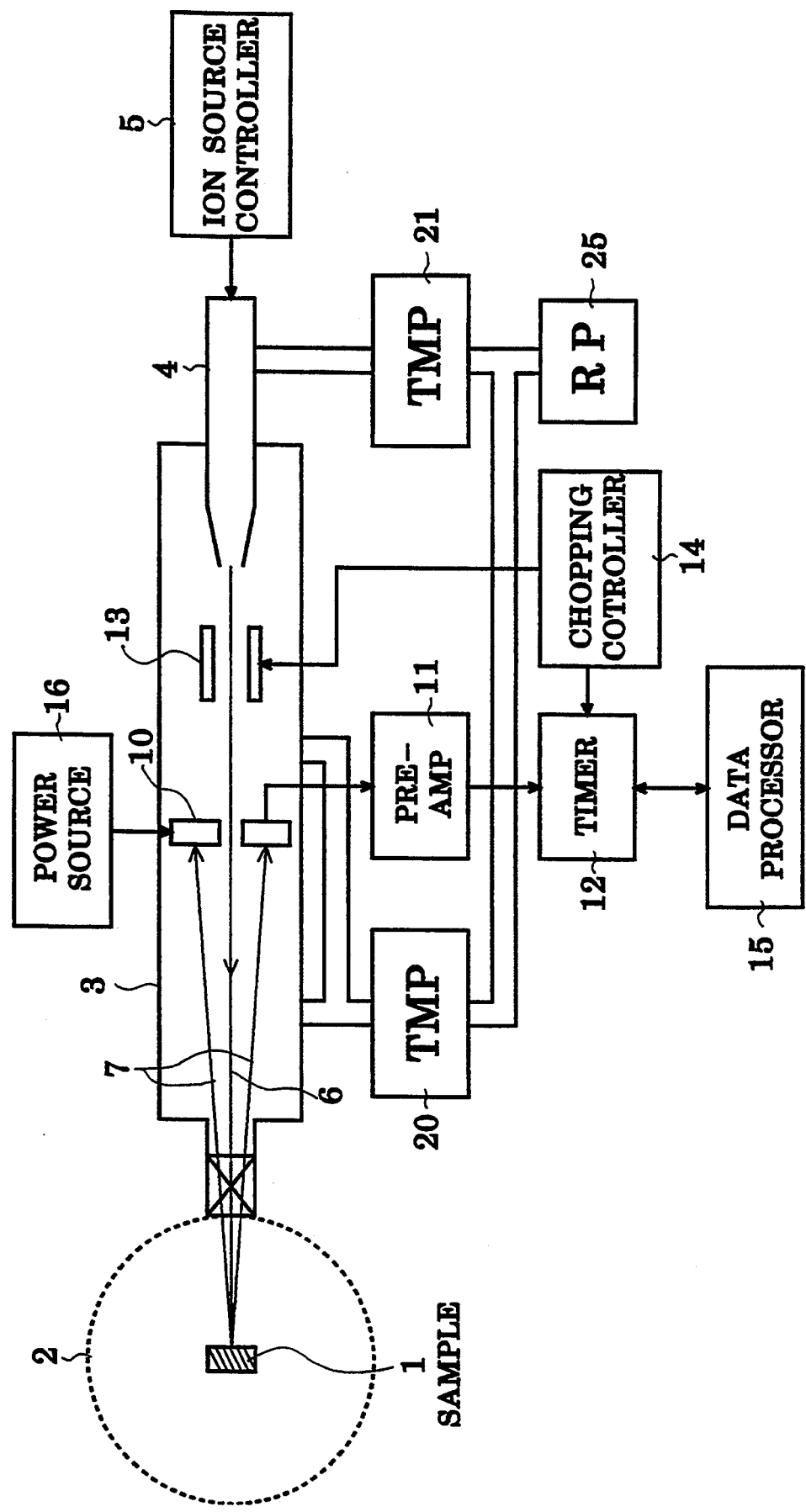
FIG. 1 is a schematic diagram of a TOF type ion scattering spectroscope of an embodiment of the present invention.
Figure 2:
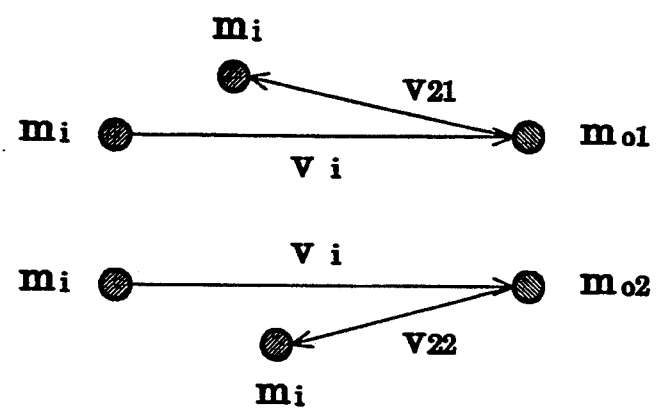
FIG. 2 is a diagram showing colliding particles.

A coaxial impact collision ion scattering spectroscope (CAICISS) embodying the present invention is described referring to FIG. 1 through 6. As shown in FIG. 1, ions are generated in an ion source 4 and ejected as a beam 6 from the ion source 4 then from a tube 3 onto a sample 1 in a sample chamber 2. After colliding with the atoms of the sample 1, the ions are scattered, and those scattered backward 7 re-enter the tube 3 and are detected by an ion detector 10. The ion source 4 is controlled by an ion source controller 5, and the ion detector 10 is powered by the power source 16. The tube 3 and the ion source 4 are evacuated by respectively provided pumps (turbo-molecular pumps 20, 21 and a rotary pump 25).

The energy spectrum of the scattered ions is observed as follows. The ion beam 6 from the ion source 4 is chopped by a pair of chopping electrodes 13 to which are applied a chopping pulse signal from a chopping controller 14. The chopping controller 14 gives a start pulse to a timer 12 at the same time as it gives the chopping pulse signal to the chopping electrodes 13, when the timer 12 starts counting time. The chopped ion beam (pulsated beam) 6 hits the sample 1 and some of the ions 7 are scattered backward to be detected by the ion detector 10 as mentioned before. When the ion detector 10 detects an ion, it gives a detection signal (a stop pulse) to the timer 12 through a pre-amp 11, by which the timer 12 stops counting time. The time interval (between the start pulse and the stop pulse) counted by the timer 12 is the time spent by the ions to fly from the chopping electrodes 13 via the sample 1 to the detector 10. The counted time (flight time) is given to a data processor 15, which calculates the energy of the ion based on the flight time and the known flight distance.

In the CAICISS of the present embodiment, the ion source 4 generates a mixture of ions of various masses. An element analysis of a sample 1 in the CAICISS of the present embodiment is now explained referring to FIGS. 4A through 4E, 5A through 5E, and 6A through 6E. Provided, for simplicity, two kinds of heavy-weight atoms and two kinds of light-weight atoms (that is, four kinds of atoms in summary) are included in the (surface of the) sample 1. The argument below is of course applicable to a greater variety of atoms.

Figure 4A:
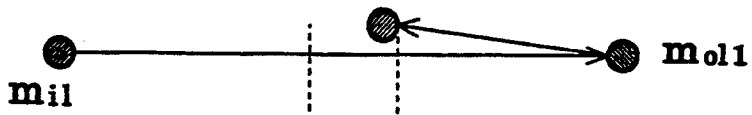
FIG. 4A through 4D are diagrams showing light-weight ions colliding with light and heavy object atoms.
Figure 4B:
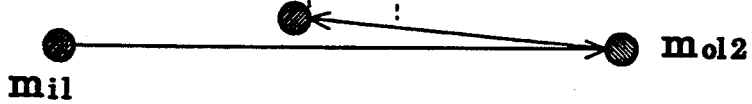

The first case refers to FIGS. 4A through 4E in which an ion lighter than the lightest atom in the (surface of the) sample 1 is used. This corresponds to the conventional case in which ions of a kind are used in the analysis. In the drawings, $m_{il}$ represents the light-weight (injecting) ion, $m_{ol1}$ represents a light-weight (object) atom, $m_{ol2}$ represents another light-weight atom but slightly heavier than the atom $m_{ol1}$, $m_{oh1}$ represents the heavy-weight atom, and $m_{oh2}$ represents another heavy-weight atom slightly heavier than the atom $m_{oh1}$. The length of the arrows corresponds to the speed of the particles. As shown by FIGS. 4A and 4B, the ion $m_{il}$ gets a slightly greater speed when it collides with the slightly heavier (light-weight) atom $m_{ol2}$ than when it collides with the slightly lighter (light-weight) atom $m_{ol1}$. The situation is explained with FIG. 2, in which $m_i$ is an injecting ion, $v_i$ is the injecting speed, $m_{o1}$ is an object atom, $m_{o2}$ is another object atom lighter than the atom $m_{o1}$, $v_{21}$ is the speed of the ion $m_i$ scattered by the heavier atom $m_{o1}$, and $v_{22}$ is the speed of the ion $m_1$ scattered by the lighter atom $m_{o2}$. Since the speeds $v_{21}$ and $v_{22}$ are given by the formula (2), the difference between them is $$v_{21}-v_{22}=2 \cdot m_i \cdot (m_{o1}-m_{o2}) \cdot v_i / \{(m_{o1}+m_i) \cdot (m_{o2}+m_1)\}, \quad (3)$$

which tells that an injecting ion $m_i$ gets a larger speed when it collides with a heavier object atom $m_{o1}$ than when it collides with a lighter atom $m_{o2}$, and the difference $v_{21}-v_{22}$ is greater as the difference in the mass of the object atoms $m_{o1}-m_{o2}$ is larger.

Figure 4C:
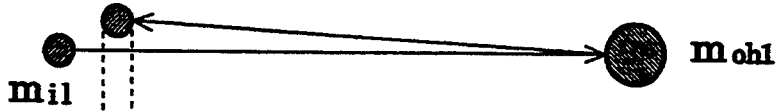
Figure 4D:
Figure 4E:
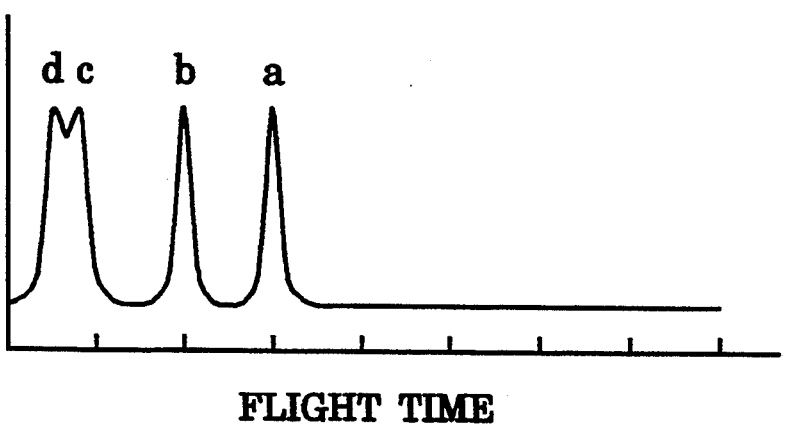
FIG. 4E is a flight time spectrum (energy spectrum) of the scattered light-weight ions.

When the number of ions is counted with respect to the flight time (which corresponds to the speed or the energy) in case of FIGS. 4A and 4B, a graph (a flight time spectrum or an energy spectrum) as shown in FIG. 4E is obtained in which the peak 'a' corresponds to the ions $m_{il}$ scattered as in FIG. 4A and the peak 'b' corresponds to the ions $m_{il}$ scattered as in FIG. 4B.

FIG. 4C shows a case in which a light-weight ion $m_{il}$ collides with a heavy-weight object atom $m_{oh1}$ and FIG. 4D shows a case in which the same ion $m_{il}$ collides with another heavy-weight atom $m_{oh2}$. In this case also the speed of the ion $m_{il}$ scattered by the slightly heavier heavy-weight atom $m_{oh2}$ gets a slightly larger speed than that scattered by the slightly lighter heavy-weight atom $m_{oh1}$. But the difference of the speeds is smaller in this case compared to the previous case (FIGS. 4A and 4B) as the mass of the object atoms are heavier and the denominator of the formula (3) is greater. Thus the peaks 'c' and 'd' of the scattered ions in the case of FIGS. 4C and 4D appear in proximity in the flight time spectrum of FIG. 4E.

In summary, light-weight object atoms $m_{ol1}$ and $m_{ol2}$ of slightly different masses can be precisely discriminated when ions having a mass smaller than the smallest mass of the atoms in the sample surface is used, but heavy-weight atoms $m_{oh1}$ and $m_{oh2}$ of slightly different masses are hardly discriminated.

Figure 5A:
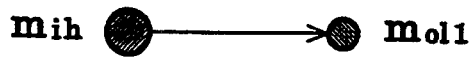
FIG. 5A through 5D are diagrams showing middle-weight ions colliding with light and heavy object atoms.
Figure 5B:
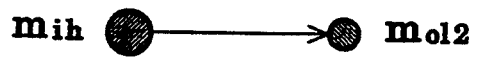
Figure 5C:
Figure 5D:

The second case refers to FIGS. 5A through 5E in which ions of an intermediate mass $m_{ih}$ is used. That is, the mass of the ions $m_{ih}$ is between the mass of the heavy-weight atoms $m_{oh1}$ and $m_{oh2}$ and the mass of the light-weight atoms $m_{ol1}$ and $m_{ol2}$. This case also corresponds to the conventional case in which ions of a kind are used in the analysis. When, as shown by FIGS. 5A and 5B, the mass of the injecting ion $m_{ih}$ is larger than the object atom $m_{ol1}$ or $m_{ol2}$, the ion is not scattered backward and no measurement is possible. When the ions collide with the heavy-weight atoms $m_{oh1}$ and $m_{oh2}$ (which are heavier than the colliding ions), they are scattered backward as shown by FIGS. 5C and 5D and the ion colliding with the slightly heavier heavy-weight atom $m_{oh2}$ gets a slightly larger speed than that colliding with the slightly lighter heavy-weight atom $m_{oh1}$ as in the previous cases.

Figure 3:
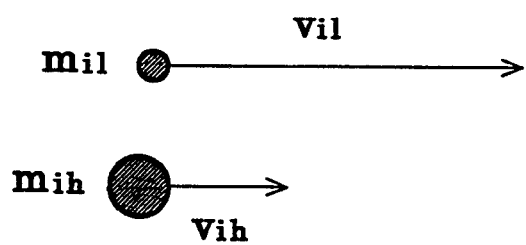
FIG. 3 is a diagram showing a relationship between the mass and speed of a particle.
Figure 5E:
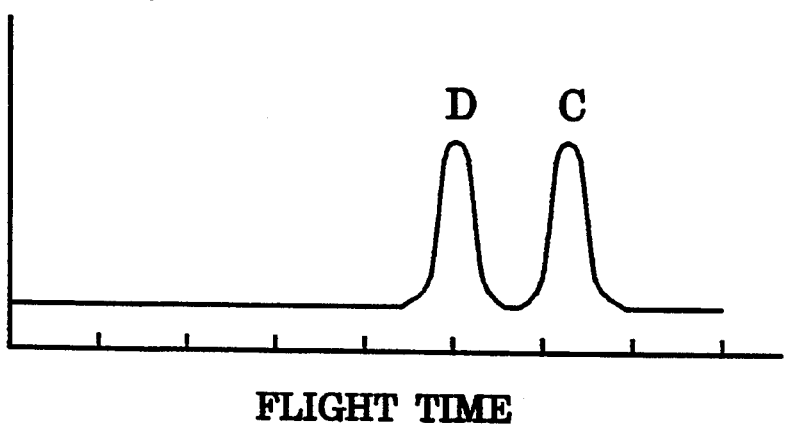
FIG. 5E is a flight time spectrum (energy spectrum) of the scattered heavy-weight ions.

The difference between the case of FIG. 4A through 4D and the case of FIGS. 5A through 5D is illustrated with FIG. 3. Since the speed of an ion is inversely proportional to the square root of the mass of the ion, the speed $v_{il}$ of a lighter ion $m_{il}$ is larger than that $v_{ih}$ of a heavier ion $m_{ih}$. Thus the speed of the heavier injecting ions $m_{ih}$ in FIGS. 5A through 5D is smaller than that of the lighter injecting ions $m_{il}$ in FIGS. 4A through 4D. This means that the flight time of the heavier (intermediate-weight) ions $m_{ih}$ is longer than that of the lighter (light-weight) ions $m_{il}$ and, as shown in FIG. 5E, the peaks 'C' and 'D' are separated and can be discriminated.

In summary, heavy-weight object atoms $m_{oh1}$ and $m_{oh2}$ can be precisely discriminated when ions having an intermediate mass between the heavy-weight atoms and light-weight atoms are used, while the light-weight atoms $m_{ol1}$ and $m_{ol2}$ are impossible to be analyzed.

The third case refers to FIGS. 6A through 6E in which mixture of ions of the first case and the second case are used. This case is the feature of the present embodiment. For the light-weight atoms $m_{ol1}$ and $m_{ol2}$ of the sample, light-weight ions $m_{il}$ work well as shown by FIGS. 6A and 6B, and the scattered ions construct distinct peaks 'a' and 'b' in the flight time spectrum of FIG. 6E. For the heavy-weight atoms $m_{oh1}$ and $m_{oh2}$ of the sample, intermediate-weight ions $m_{ih}$ work well as shown by FIGS. 6C and 6D, and the scattered ions construct distinct peaks 'C' and 'D'.

Thus, in the CAICISS of the present embodiment using a mixture of ions of such masses (i.e., $[m_{il}] < [m_{ol1},$ $m_{o12}] \leq [m_{ih}] < [m_{oh1}, m_{oh2}]$), atoms of any mass in the sample surface can be precisely analyzed. When, for example, elements such as C or O adsorbing on a GaAlAs substrate is to be analyzed, a mixture of He and Ar gases can be used as the ion source (in which case, [He]<[C, O, Al]<[Ar]<[Ga, As]).

Figure 7:
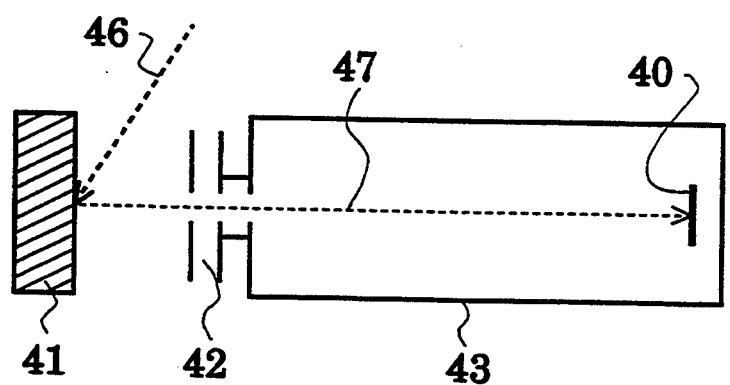
FIG. 7 is a cross sectional view of a sample and a flight tube receiving ions scattered by the sample.
Figure 8:
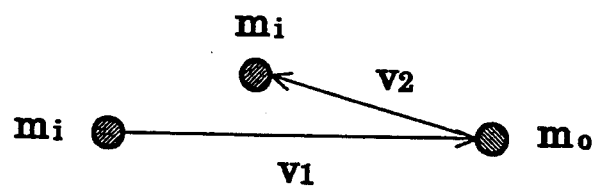
FIG. 8 is a diagram showing colliding particles.

Though, in the above description, a CAICISS is taken as an example for simplicity of explanation and calculation of kinematics, the present invention is applicable to any kind of TOF type ISS other than the coaxial impact collision type including the type of ISS shown in FIG. 7.

What is claimed is:

1. An ion scattering spectroscope comprising:
   an ion source for generating and ejecting a mixture of ions of different known masses from an ion source material;
   an ion detector for detecting ions ejected from the ion source after the ions have collided with atoms about a sample and been scattered by the sample atoms, the mixture of ions including:
      a) ions of a mass smaller than a mass of the lightest of the sample atoms, and
      b) ions of another mass larger than the mass of the lightest of the sample atoms, and smaller in mass than the heaviest of the sample atoms; and
   a timer measuring a time interval from a certain time point before collision with the sample atoms until the ions are detected by the ion detector.

2. The ion scattering spectroscope according to claim 1, wherein the ion source material is a gas.

3. The ion scattering spectroscope according to claim 1, wherein the ion source material is a solid.

4. An ion scattering spectroscope comprising:
   an ion source for generating a mixture of ions of different known masses from an ion source material and for ejecting the ions as a beam;
   a beam chopper for chopping the beam of ions and for passing a short beam of ions;
   an ion detector for detecting ions passing through the beam chopper after the ions have collided with atoms about a sample and been scattered by the sample atoms, the ion beam including:
      a) ions of a mass smaller than a mass of the lightest of the sample atoms, and
      b) ions of another mass larger than the mass of the lightest of the sample atoms, and smaller in mass than the heaviest of the sample atoms; and
   a timer measuring a time interval from a time when the short beam of ions passes through the beam chopper until a time when the ions are detected by the ion detector.

5. The ion scattering spectroscope according to claim 4, where the ion detector is positioned between the ion source and the sample, the ion detector having a hole for allowing the beam of ions to pass as the ion beam propogates towards the sample, and the ion detector detecting back-scattered ions from the sample.

6. The ion scattering spectroscope according to claim 4, wherein the ion source material is a gas.

7. The ion scattering spectroscope according to claim 4, wherein the ion source material is a solid.

8. The ion scattering spectroscope according to claim 4, wherein the beam chopper includes a pair of electrodes to which is applied a pulse voltage signal.

* * * * *